(12) United States Patent
Hubert et al.

(10) Patent No.: US 7,878,203 B2
(45) Date of Patent: Feb. 1, 2011

(54) PHOTOTHERAPEUTIC TREATMENT METHOD USING A PASSIVE HOST MEDIUM CONTAINING NANOPARTICLES

(75) Inventors: Manfred Hubert, Toronto (CA); Steven Martin, Toronto (CA); Ben G. Yacobi, Mississauga (CA); Thomas A.D. Burgmann, Mississauga (CA); Philip W. Passy, Hartwell, GA (US)

(73) Assignee: MedX Health Corp., Mississauga, Ontario (CA)

( * ) Notice: Subject to any disclaimer, the term of this patent is extended or adjusted under 35 U.S.C. 154(b) by 1574 days.

(21) Appl. No.: 11/007,597

(22) Filed: Dec. 9, 2004

(65) Prior Publication Data

US 2005/0182461 A1    Aug. 18, 2005

Related U.S. Application Data

(60) Provisional application No. 60/527,521, filed on Dec. 9, 2003.

(51) Int. Cl.
*A61B 19/00* (2006.01)
*A61N 5/06* (2006.01)

(52) U.S. Cl. ........................................ 128/898; 607/88
(58) Field of Classification Search ............. 607/88–95; 606/4–28; 128/898
See application file for complete search history.

(56) References Cited

U.S. PATENT DOCUMENTS

| | | | | |
|---|---|---|---|---|
| 5,990,479 A | * | 11/1999 | Weiss et al. | 250/307 |
| 6,290,713 B1 | * | 9/2001 | Russell | 607/88 |
| 7,083,610 B1 | * | 8/2006 | Murray et al. | 606/9 |
| 7,239,072 B2 | * | 7/2007 | Snijkers-Hendrickx et al. | 313/493 |
| 7,294,417 B2 | * | 11/2007 | Ren et al. | 428/701 |

OTHER PUBLICATIONS

Bhargava et al.; "Doped nanocrystals of semiconductors—a new class of luminescent materials"; Journal of Luminescence 60&61, 1994, pp. 275-280; Elsevier Science B.V.
Yoffe; "Semiconductor quantum dots and related systems: electronic, optical, luminescence and related properties of low dimensional systems"; Advances in Physics, 2001, vol. 50, No. 1, pp. 1-208; Taylor & Francis Ltd.
Dabbousi et al.; (CdSe)ZnS Core-Shell Quantum Dots: Synthesis and Characterization of a Size Series of Highly Luminescent Nanocrystallites; J. Phys. Chem. B, 101; pp. 9463-9475; 1997; American Chemical Society.
Alivisatos; "Nanocrystals: building blocks for modern materials design"; Endeavour vol. 21(2); pp. 56-60; 1997; Elsevier Science Ltd.
Bruchez, Jr. et al.; "Semiconductor Nanocrystals as Fluorescent Biological Labels"; Science, vol. 281; pp. 2013-2016; Sep. 25, 1998.
Murray et al.; "Synthesis and Characterization of Monodisperse Nanocrystals and Close-Packed Nanocrystal Assemblies"; Annu. Rev. Mater. Sci. 30; pp. 545-610; 2000; Annual Reviews.

* cited by examiner

*Primary Examiner*—Ahmed M Farah
(74) *Attorney, Agent, or Firm*—Shoemaker and Mattare

(57) ABSTRACT

A method of making shape-adaptable and spectral-selective distributed optical radiation sources, in the wavelength range between UV and mid-infrared, for therapeutic treatment using passive host medium containing nanocrystals is disclosed. The spectral output of the distributed optical radiation source is controlled by the nanocrystal size distribution that determines the spectral output of fluorescence radiation originating from these nanocrystals from within the said host medium, which contains the said nanocrystals, under excitation by an external source. The size of nanocrystals, or the size distribution of nanocrystals, incorporated in the host medium is selected based on the radiation spectral output required for therapeutic requirements. The passive host medium, incorporating the said nanocrystals, is made of adaptable, geometrically configurable, material that conforms to any desired shape.

34 Claims, 5 Drawing Sheets

GEL PACK    REPLACEABLE DISC
CONTAINING NANOPARTICLES

PHOTOTHERAPEUTIC TREATMENT METHOD USING A PASSIVE HOST MEDIUM CONTAINING NANOPARTICLES

This application claims benefit of provisional application No. 60/527,521, filed Dec. 9, 2003.

BACKGROUND OF THE INVENTION

1. Field of the Invention

The present invention relates to a method of making shape-adaptable and spectral-selective distributed optical radiation source for therapeutic treatment using passive host mediums containing nanocrystals.

2. Description of the Prior Art

The therapeutic effects of light therapy, or phototherapy, have been recognized since ancient times. At present, therapeutic treatment with light and specific color is a widely accepted methodology in various applications. In general, therapeutic light treatment employing low-intensity irradiation is primarily employed in the treatment of skin diseases and physiological problems, such as, carpal tunnel syndrome, tendonitis, rheumatoid arthritis, low back pain, and general pain control. Photo-therapeutic treatment typically affects photoreceptors in the tissue, with consequent alterations in the biochemical processes of the cells. This is accompanied by an increase in local blood circulation and a strengthening of the immune defense system. It has been extensively demonstrated that the use of monochromatic light results in (i) increased flow of oxygen and blood, (ii) decreased inflammation, and (iii) muscle relaxation and pain reduction. Thus, it is widely accepted that absorbed light triggers biological changes within the body, and in such cases, the use of specific wavelengths of light accelerates cellular metabolic processes and stimulates vital chemical reactions. Specifically, light therapy can, for example, (i) increase the circulation by promoting the formation of new capillaries, which accelerate the healing process, (ii) increase DNA/RNA synthesis, which assists damaged cells to be replaced more rapidly, (iii) stimulate collagen protein production, which is important for repairing damaged tissue and replacing old tissue and (vi) shift the cellular redox state which increases pHi toward a more oxidized state when previously it was below optimal for cellular response.

In relation to the foregoing discussion, it is important to note that both visible, especially red, and near-infrared light have been demonstrated to influence many changes at a cellular level. In general, the various tissue and cell types have their own specific light absorption characteristics. In other words, they absorb light at specific wavelengths only. For typically employed wavelength range of 600 to 900 nm, the radiation is absorbed closer to the surface for shorter wavelengths, whereas for longer wavelengths the penetration depth is greater.

It should also be emphasized at this juncture that, as various studies demonstrate, the results of phototherapy are related to the application of light at specific wavelengths and intensities, rather than to coherence effects.

In many cases of light therapy, a careful selection of the spectral content of light used for treatment is of great importance. There were numerous studies confirming the importance of selecting a specific wavelength for light treatment to be optimal. The primary aspect of light therapy is related to cellular regeneration as the result of action of light with the suitable wavelengths and the accurate prescribed doses. Such light therapies typically employ the wavelengths in the range between about 400 and 1500 nanometers, with different wavelengths of light having diverse effects. Whereas the use of lasers (coherent light) has become ubiquitous in various fields in medicine, non-coherent light therapies, employing light-emitting diodes (LEDs) has been proliferating in the past years as well. Typically, wavelengths in the visible range (400-700 nm) and the near-infrared region (700-1000 nm) of the electromagnetic spectrum are employed in light therapies. However, in the context of providing distributed light sources, which are suitable to conform with various body parts during light therapy, lasers and even LED arrays do not provide conformal and adaptable distributed light sources. On the other hand, lasers and LEDs provide high efficiencies. Thus, it would be highly desirable to provide a method of shape-adaptable and spectral-selective distributed optical radiation sources for therapeutic treatment using passive host medium containing nanocrystals that are excited by the said lasers or LEDs. In such a case, the spectral output of the distributed optical radiation source is controlled by the nanocrystal size distribution that determines the spectral output of fluorescence radiation originating from these nanocrystals from within the said host medium, which contains the said nanocrystals, under excitation by an external source. The said host medium, incorporating nanocrystals, can be made of adaptable, geometrically configurable, material that conforms to any desired shape.

Thus, in relation to the foregoing discussion, it is desirable to have a capability of selecting the spectral output and intensity of the optical radiation source according to specific therapeutic requirements. It would also be very advantageous to provide a method of providing an adaptable light-source medium, which can be configured both geometrically and spectrally, and which provides wavelength tunability for therapeutic treatment.

SUMMARY OF THE INVENTION

It is an object of the present invention to present a method of providing radiation treatment with desired spectral content for therapeutic purposes by incorporating into the host medium nanocrystals which when irradiated by an external excitation source responsively emit radiation in the desired wavelength region thereby acting in effect as a plurality of light sources within the host itself.

More specifically the present invention provides a method of spectral-selective optical therapeutic treatment in the wavelength range between UV and mid-infrared.

In one aspect of the invention there is provided a method for therapeutic treatment with light, comprising;

using as a light source passive host medium containing nanocrystals, which emit electromagnetic radiation responsive to being irradiated by an external excitation source; and irradiating said passive host medium containing nanocrystals with emissions from an effective excitation source for an effective period of time, wherein said nanoparticles emit electromagnetic radiation for therapeutic treatment.

The passive host light-source medium, incorporating the said nanocrystals, is made of adaptable, geometrically configurable, material that conforms to any desired shape. Specifically, a shape-adaptable (conforming to a body part or surrounding various body parts) passive host light-source medium is selected, but not limited, to gel packs, liquid bags, and solid replaceable discs, or other solid preformed shapes for specific applications, which are all pumped by an LED or LED array, or LED (or Laser)-pumped optical fibers; the said medium conforming to shapes such as knee or elbow or face, or any other body part requiring light treatment; specifically, the said medium can wrap around joints (e.g., wrist, elbow, knee), delivering light through a surrounding field of irradiation.

It is important to emphasize that, providing sufficient energy in order to produce a beneficial effect on the irradiated area, the said host light-source medium is not expected to deliver excessive power resulting in damage of the tissue. Thus, the host light-source medium is expected to provide a softer delivery of the light at healing wavelengths, as compared to, for example, high-power focused LASER or incandescent lamp source. In addition, unlike single-wavelength sources, the said host light-source medium can provide a broad multiplicity of wavelengths and thus affect both a wider range of tissue types and generate a broader range of responses in the tissue.

BRIEF DESCRIPTION OF THE DRAWINGS

Preferred embodiments of the invention will now be described, as an example only, with reference to the drawings, in which.

DETAILED DESCRIPTION OF THE INVENTION

Figure 1:
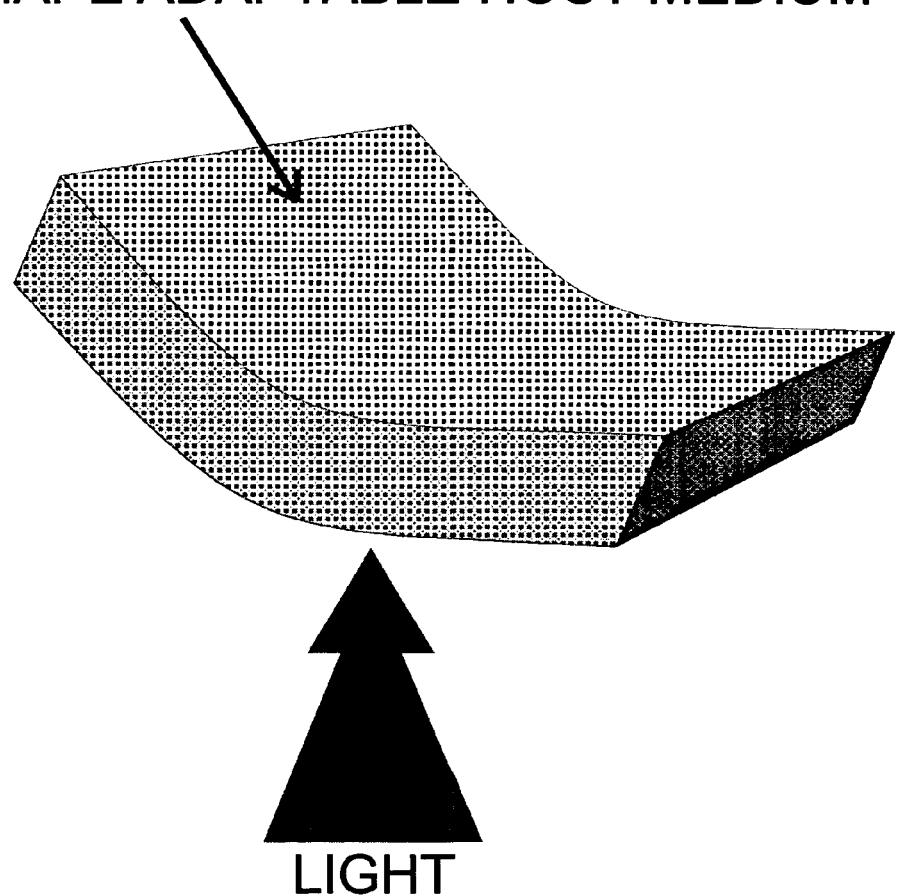
FIG. 1 shows a host light-source medium, impregnated with nanoparticles in accordance with the present invention.
Figure 2:
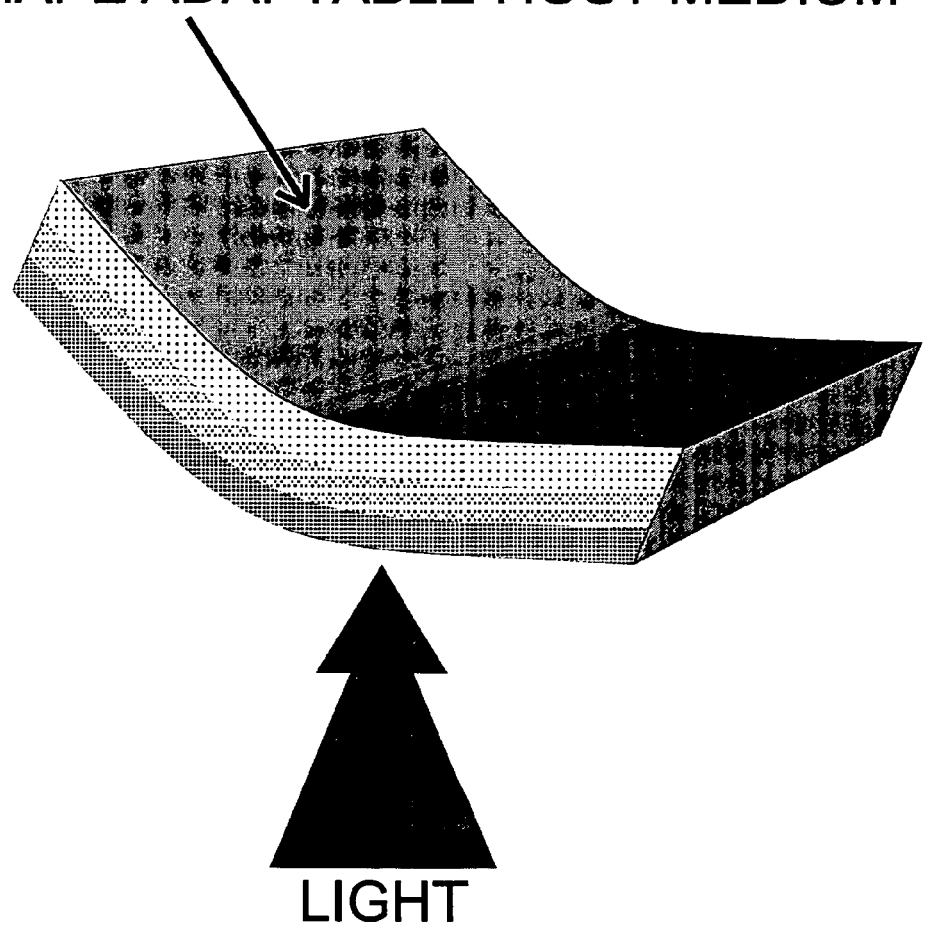
FIG. 2 shows a non-uniform distribution of fluorescing nanoparticles to take into account absorption of light by the host medium.
Figure 3:
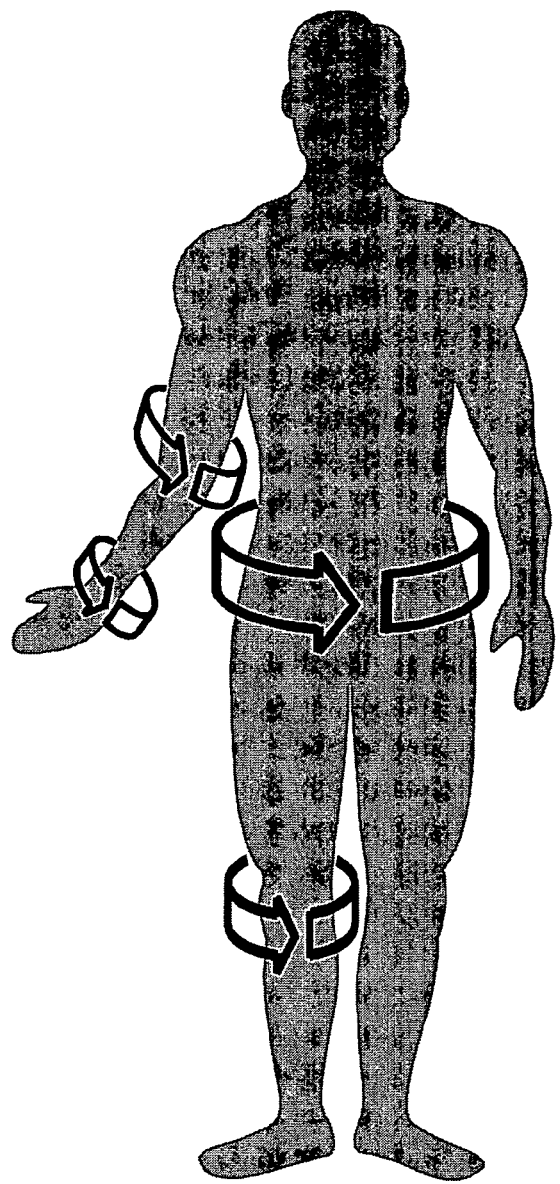
FIG. 3 shows examples of application of the host light-source medium adapted to the human wrist, elbow, arm, knee, leg and face.
Figure 4:
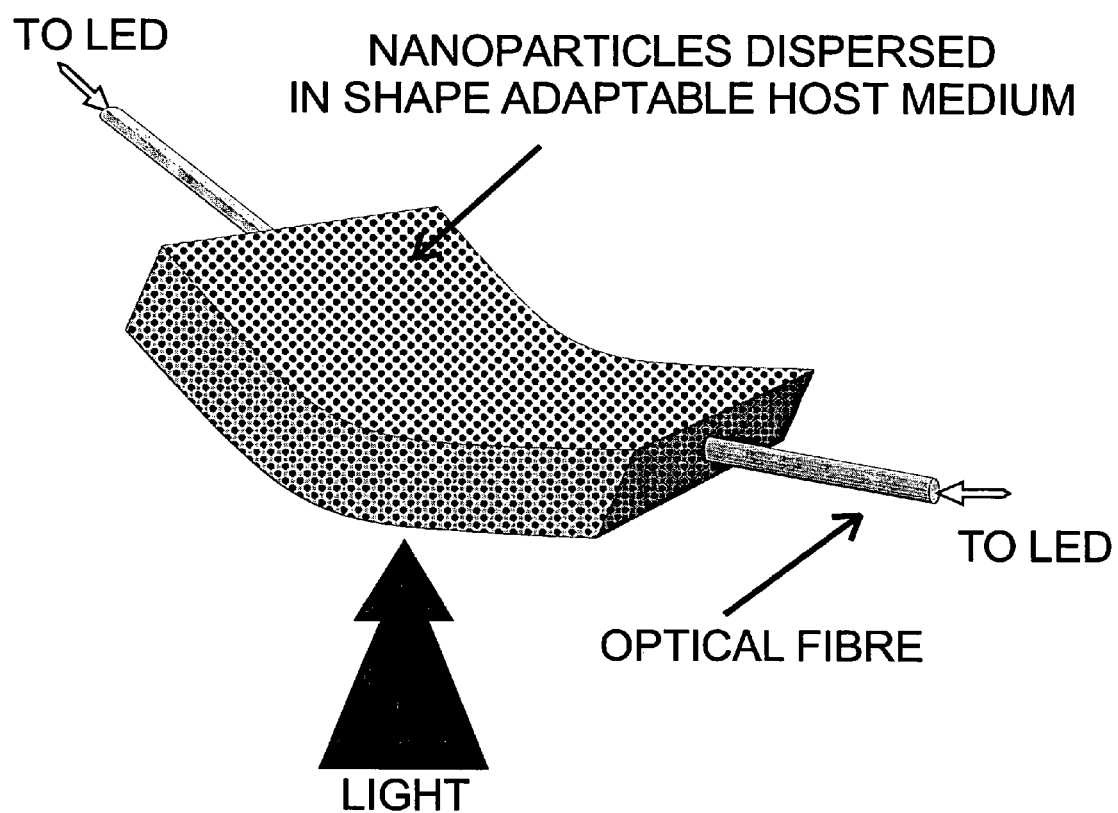
FIG. 4 shows an example of application of the host light-source medium containing nanocrystals that are excited by LED pumped optical fibers.
Figure 5:
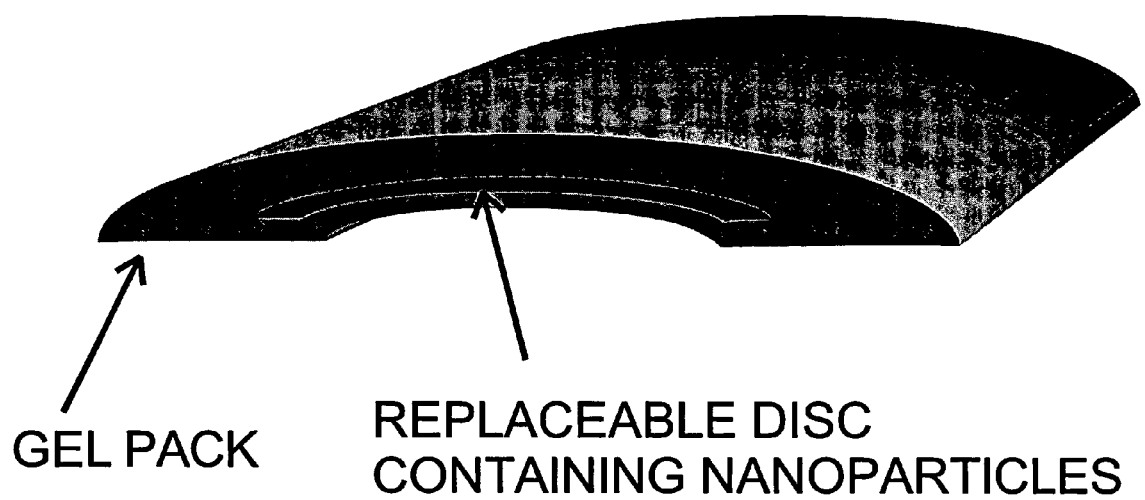
FIG. 5 shows an example of application of the gel pack incorporating a solid replaceable disk containing nanocrystals.

The present method involves incorporating nanocrystals into a passive host medium, and when irradiated by an excitation source, the said nanocrystals responsively emit radiation in the desired wavelength region thereby acting as a light source within the said host medium. The term passive host medium means a medium which can emit radiation responsive to some form of excitation energy, but which does not require any electronics or power associated with it.

Also, as used herein, the term "nanocrystals" means nanoparticles, which can emit radiation responsive to some form of excitation energy. Thus it will be understood that the term "nanocrystals" as used herein is not restricted to crystalline structures, although crystalline nanoparticles such as crystalline semiconductor nanocrystals are a preferred embodiment. However, noncrystalline semiconductor nanoparticles and other inorganic or organic nanoparticles may also be used.

Semiconductor nanocrystals are described in the references listed in the section entitled References Cited. These nanocrystals are capable of emitting optical radiation within a narrow wavelength depending on the size of the nanocrystals. These nanocrystals are also referred to in the literature as quantum dots.

In general, nanocrystals have dimensions between about 1 nm and 50 nm, and their structural properties, such as lattice structure and bond spacing are similar to a macroscopic counterpart of the material. Nanocrystals exhibit quantum size effect, which arise when their size is commensurate with de Broglie wavelength of an elementary particle (e.g., electron, or hole, or an exciton). Due to the quantum size effect, semiconductor nanocrystals exhibit discrete optical transitions as the result of the confinement of the electron-hole pairs, and their optical properties are strongly dependent on the size of the nanocrystal, with the onset of absorbance and maximum of fluorescence spectrum being shifted to higher energy with decreasing size. The types of nanocrystals can be listed as follows: materials such as CuCl, AgBr, or NaCl; materials such as HgS, HgSe, HgTe, CdSe, CdS, CdTe, ZnSe, ZnTe, ZnO, ZnS, or alloys of these materials; materials such as PbS, PbSe, PbTe, or alloys of these materials; materials such as GaP, GaAs, InP, InAs, InSb, or alloys of these materials; materials such as C, Si, Ge, or alloys of these materials; metals such as Ni, Cu, Ag, Pt, or Au; or metal oxides such as silica, titania, alumina, or zirconia.

The synthesis and various applications of the said nanocrystals are described in several papers and U.S. Patents. For example, the synthesis of nanocrystalline II-VI and III-V compounds is described by Alivisatos et al. in U.S. Pat. Nos. 5,262,357, 5,505,928, and 5,751,018; specifically, U.S. Pat. No. 5,751,018 describes methods for attaching nanocrystals to solid inorganic surfaces by employing "self-assembled bifunctional organic monolayers as bridge compounds". Another example of the preparation of various III-V semiconductors was described by Nozik et al. (MRS Bulletin vol. 23, pp. 24-30, February 1998) for InAs, InP, GaAs, and GaP, which can be formed into powders or suspended in solids such as polymers and glasses. Yet another example of the preparation of various monodisperse nanocrystals and close-packed nanocrystal assemblies was described by Murray et al. (Annual Review of Materials Science, Vol. 30, pp 545-610, 2000).

One preferable type of nanocrystal that may be used are those having core/shell configuration, i.e. a system with one semiconductor nanocrystal forming a core and with another semiconductor forming a shell (of one to several monolayers thick) over the core nanocrystal. This results in passivating the surface of the core nanocrystal leading to a substantial enhancement in the emission of optical radiation. As an example, formation of CdS layer over a CdSe core results in a significant enhancement of the luminescence quantum yield (see, for example, Alivisatos, A. P., MRS Bulletin, vol. 23, pp. 18-23, February 1998).

The semiconductor nanocrystals embedded in a polymer matrix may have utility in areas, such as optical modulators and switches for use in telecommunications systems, described in U.S. Pat. No. 6,005,707. Luminescent semiconductor nanocrystals can be also employed as probes for biological applications, as described in U.S. Pat. No. 5,990,479. The utility of doped nanocrystals, such as ZnS doped with a manganese luminescent center, was described by Bhargava et al. (Journal of Luminescence, Vols. 60 and 62, pp. 275-280, 1994). Research and various applications of the nanocrystals are also discussed, for example, in MRS Bulletin (Volume 23, No. 2, February 1998).

It is noted that, although the luminescent semiconductor nanocrystals can be excited over a wide wavelength range, they emit optical radiation in a relatively narrow wavelength band. In principle, the nanocrystals can be excited by the optical radiation (i.e., UV, visible, and infrared), as well as by x-rays or by the irradiation with an electron beam. The important feature of the excitation of the nanocrystals having different sizes is that one source can lead to the concurrent excitation of all of the nanocrystals, and thus result in the narrow-band emission of the optical radiation at different wavelengths, which are tunable by selecting the appropriate size distribution of the said nanocrystals.

When the host light-source medium containing nanocrystals is under optical irradiation with a photon energy exceeding the magnitudes of the energy gap of all (or in some cases, some) of the nanocrystals having different sizes, each of these nanocrystals will fluoresce at a characteristic wavelength corresponding to the specific size of the nanocrystal. The emission can be tuned by selecting the mean size, or size distribution, of the nanocrystals. Thus, the spectral content of the fluorescence, originating within the host light-source medium, can be also tuned or selected a priori, by incorporating a given size—distribution of nanocrystals.

As described above, nanocrystals have typical dimensions between about 1 nm and 10 nm and they exhibit quantum size effects, i.e., semiconductor nanocrystals exhibit discrete optical transitions as the result of the confinement of the electron-hole pairs, and their optical properties are strongly dependent on the size of the nanocrystal, with the onset of absorbance and maximum of fluorescence spectrum being shifted to higher energy with decreasing size.

The sizes of nanocrystals that are incorporated in the host light-source medium are preferably between 1 and 100 nm, and more preferably between 1 and 50 nm, and in most preferable cases, for achieving quantum size effects, between 1 and 10 nm.

In summary, a method of shape-adaptable and spectral-selective distributed optical radiation sources, in the wavelength range between UV and mid-infrared, for therapeutic/cosmetic treatment using passive host light-source medium containing nanocrystals is disclosed. The spectral output of the distributed optical radiation source is controlled by the nanocrystal size distribution that determines the spectral output of fluorescence radiation originating from these nanocrystals from within the said host medium that contains the said nanocrystals. The size of nanocrystals (or the size distribution of nanocrystals) incorporated in the host medium is selected based on the radiation spectral output required for therapeutic requirements. The passive host medium, incorporating the said nanocrystals, is made of adaptable (geometrically configurable) material that conforms to any desired shape. The nanocrystals incorporated in the host light-source medium are excited by a solid-state laser or LED. In such a case, the spectral output of the distributed optical radiation source is controlled by the nanocrystal size distribution that determines the spectral output of fluorescence radiation originating from these nanocrystals from within the said host medium, which contains the said nanocrystals, under excitation by an external source.

What is claimed is:

1. A method comprising;
   incorporating into a passive host medium nanoparticles that emit electromagnetic radiation in response to being irradiated by an external excitation source, the host medium being formed of geometrically configurable material thereby to enable the passive host medium to conform generally to the shape of a target region of a subject to be therapeutically treated, the nanoparticles being distributed generally throughout said passive host medium;
   bringing said host medium into proximity to said target region with said host medium substantially conforming to the shape of said target;
   subjecting the host medium to radiation emitted by the external excitation source to excite the nanoparticles; and
   irradiating the target region of said subject with electromagnetic radiation emitted by the distributed nanoparticles generally throughout said passive host medium for an effective period of time, wherein said nanoparticles emit electromagnetic radiation for therapeutic purposes and at a therapeutically effective level thereby to treat said subject.

2. The method according to claim 1, wherein said electromagnetic radiation emitted by said nanoparticles is fluorescence, and wherein said nanoparticles have a mean size selected so that said fluorescence has a wavelength in a preselected wavelength range.

3. The method according to claim 1, wherein said host medium is selected from the group consisting of a gel pack, a cream-filled bag, a powder-filled bag, a solid malleable object, or a liquid-filled bag.

4. The method according to claim 1, wherein the external excitation source is an x-ray source.

5. The method according to claim 1, wherein said nanoparticles have a distribution gradient through said host medium that is selected to ensure uniform generation of light through the bulk of the host medium by said nanoparticles when irradiated by said external excitation source.

6. The method according to claim 5, wherein said light has a wavelength in a wavelength range between ultraviolet and infrared.

7. The method according to claim 5, wherein said light has a wavelength in the visible range.

8. The method according to claim 5, wherein said light has a wavelength in the infrared range.

9. The method according to claim 1, wherein said nanoparticles are semiconductor nanocrystals selected from the group consisting of CuCl, AgBr, NaCl, HgS; HgSe, HgTe, CdSe, OdS, CdTe, ZnSe, ZnTe, ZnO, ZnS, or alloys of these materials; PbS, PbSe, PbTe, or alloys of these materials; GaP, GaAs, InP, InAs, InSb, or alloys of these materials; C, Si, Ge, or alloys of these materials.

10. The method according to claim 9, wherein the semiconductor nanoparticles contain dopants.

11. The method according to claim 9, wherein multiple sized nanoparticles are incorporated in the passive host medium.

12. The method according to claim 11, wherein the sizes of nanoparticles that are incorporated in the passive host medium are between 1 and 100 nm in diameter.

13. The method according to claim 1, wherein a plurality of different types of nanoparticles of various sizes are incorporated into the host medium.

14. The method according to claim 13, wherein sizes of said nanoparticles are selected so as to provide various combinations of visible light, visible and infrared light, or infrared light.

15. The method according to claim 1 wherein each nanoparticle has a diameter in the range of 1 nm to 100 nm.

16. The method according to claim 15 wherein each nanoparticle has a diameter in the range of 1 nm to 50 nm.

17. The method of according to claim 16 wherein each nanoparticle is of the same diameter.

18. The method according claim 17 wherein each nanoparticles is formed of the same material.

19. The method according to claim 17 wherein nanoparticles formed of differing material are incorporated within said host medium.

20. The method according to claim 17, wherein said nanoparticles have a distribution gradient through said host medium that is selected to ensure uniform generation of light through the bulk of the host medium by said nanoparticles when irrodiated by said external excitation source.

21. The method according to claim 16 wherein nanoparticles of different diameters are incorporated with said host medium.

22. The method according claim 21 wherein each nanoparticles is formed of the same material.

23. The method according to claim 21 wherein nanoparticles formed of differing material are incorporated within said host medium.

24. The method according to claim 21, wherein said nanoparticles have a distribution gradient through said host medium that is selected to ensure uniform generation of light through the bulk of the host medium by said nanoparticles when irrodiated by said external excitation source.

25. An optical radiation therapeutic treatment method comprising:
bringing a geometrically configurable host medium having nanparticles distributed therein in proximity to a region of a subject to be treated and conforming the host medium generally to the shape of said region;
subjecting the host medium to radiation emitted by an external excitation source selected to excite said nanoparticles; and
irradiating the region of said subject with electromagnetic radiation emitted by said excited nanoparticles.

26. The method according to claim 25, wherein said electromagnetic radiation emitted by said nanoparticles is fluorescence, and wherein said nanoparticles have a mean size selected so that said fluorescence has a wavelength in a preselected wavelength range.

27. The method according to claim 26, wherein said nanoparticles have a distribution gradient through said host medium that is selected to ensure uniform generation of light through the bulk of the host medium by said nanoparticles when irradiated by said external excitation source.

28. The method according to claim 27, wherein said nanoparticles are semiconductor nanocrystals selected from the group consisting of CuCI, AgBr, NaCI, HgS; HgSe, HgTe, CdSe, OdS, CdTe, ZnSe, ZnTe, ZnO, ZnS, or alloys of these materials; PbS, PbSe, PbTe, or alloys of these materials; GaP, GaAs, InP, InAs, InSb, or alloys of these materials; C, Si, Ge, or alloys of these materials.

29. The method according to claim 28, wherein the semiconductor nanoparticles contain dopants.

30. The method according to claim 28 wherein each nanoparticle has a diameter in the range of 1 nm to 100 nm.

31. The method of according to claim 30 wherein each nanoparticle is of the same diameter.

32. The method according to claim 30 wherein nanoparticles of different diameters are incorporated with said host medium.

33. The method according claim 30 wherein each nanoparticles is formed of the same material.

34. The method according to claim 30 wherein nanoparticles formed of differing material are incorporated within said host medium.

* * * * *